United States Patent [19]

Coates et al.

[11] Patent Number: 6,090,308
[45] Date of Patent: *Jul. 18, 2000

[54] DIREACTIVE MESOGENIC COMPOUNDS AND INTERMEDIATES

[75] Inventors: David Coates; Simon Greenfield, both of Dorset, United Kingdom

[73] Assignee: Merck Patent Gesellschaft, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/875,767

[22] PCT Filed: Jan. 22, 1996

[86] PCT No.: PCT/EP96/00240

§ 371 Date: Aug. 5, 1997

§ 102(e) Date: Aug. 5, 1997

[87] PCT Pub. No.: WO96/24647

PCT Pub. Date: Aug. 15, 1996

[30] Foreign Application Priority Data

Feb. 6, 1995 [GB] United Kingdom .................. 9502294
Sep. 15, 1995 [EP] European Pat. Off. .............. 95114518

[51] Int. Cl.[7] .......................... C09K 19/12; C09K 19/20; C09K 19/52

[52] U.S. Cl. ................................ 252/299.65; 252/299.66; 252/299.67; 252/299.01

[58] Field of Search .......................... 252/299.01, 299.66, 252/299.67, 299.65

[56] References Cited

U.S. PATENT DOCUMENTS

| | | | |
|---|---|---|---|
| 5,210,630 | 5/1993 | Heyderickx et al. | 359/106 |
| 5,401,437 | 3/1995 | Im | 252/299.01 |
| 5,567,349 | 10/1996 | Kelly et al. | 252/299.01 |
| 5,593,617 | 1/1997 | Kelly et al. | 252/299.67 |
| 5,622,648 | 4/1997 | Parri et al. | 252/299.66 |
| 5,641,426 | 6/1997 | Nerad et al. | 252/299.01 |
| 5,833,880 | 11/1998 | Siemensmeyer et al. | 252/299.64 |

FOREIGN PATENT DOCUMENTS

| | | |
|---|---|---|
| 405713 | 1/1991 | European Pat. Off. . |
| 93/22397 | 11/1993 | WIPO . |

*Primary Examiner*—C. H. Kelly
*Attorney, Agent, or Firm*—Millen, White, Zelano & Branigan, P.C.

[57] ABSTRACT

The invention relates to direactive mesogenic compounds or mixtures thereof comprising mesogene-containing molecules, said mesogens having two side chains attached thereto which contain a terminal polymerizable functional group, said mesogens and said functional groups being separated by spacer groups having at least two to twenty spacer atoms, wherein both spacer groups have different chain length.

23 Claims, No Drawings

DIREACTIVE MESOGENIC COMPOUNDS AND INTERMEDIATES are mentioned in EP 0,261,712 (n=o), EP 0,331,233 (n=1). Reactive liquid crystal biphenyls of formula

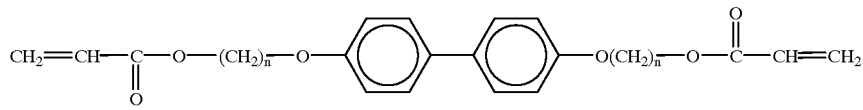

The invention relates to direactive mesogenic compounds or mixtures thereof obtainable by a) treating a mesogenic diol of formula I,

HO-MG-OH  (I)

in which are disclosed by EP 0,405,713.

The International Patent application WO 93/22397 discloses a compound of formula

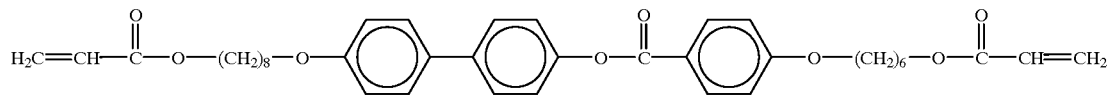

MG is a mesogenic group,
with a mixture of the halides of formula II and III,

$X^1$—$(CH_2)_m$—$R^a$  (II)

$X^2$—$(CH_2)_n$—$R^b$  (III)

in which
$X^1$ and $X^2$ are each independently Cl, Br or I,
m and n are different integers between 1 and 20
$R^a$ and $R^b$ are each independently groups selected from
—$CH_2OH$ or —CH=CWH
wherein
W is H, $CH_3$ or Cl,
in the presence of a base, and b) treating the resulting intermediate
in the case of $R^a$ and $R^b$ being —$CH_2OH$, with a vinyl derivative of formula $CH_2$=CW—$(CO)_a$—O— or a reactive derivative thereof, in which a is 0 or 1
in the case of $R^a$ and $R^b$ being CH=CWH with a perbenzoic acid.

The invention furthermore relates to the preparation of such compounds and to their use in electrooptical scattering systems and for the preparation of oriented liquid crystal polymers.

Reactive liquid crystal compounds can be polymerized in situ, whilst in their liquid crystal phase, to give highly crosslinked anisotropic films which can be used, for example, as polarizing beam splitters (see, for example, EP 0,428,213). Reactive liquid crystal compounds have furthermore been proposed for electrooptical scattering systems (see, for example, EP 0,451,905), cholesteric polarizers (e.g. EP 0,606,940) and compensation films for STN displays (e.g. EP 0,423,881).

Reactive liquid crystal diesters of formula

These reactive liquid crystalline compounds often exhibit, however, rather high melting points disadvantageous values of the birefringence and comparable narrow mesophase ranges.

In view of the broad range of applications of reactive liquid crystal compounds it was desirable to have available further compounds of this type which fulfill the various requirements such as a reasonably low melting point, a high birefringence, a broad mesogenic range and preferably an enantiotropic nematic range to a high degree.

It was an object of the present invention to provide new reactive liquid crystalline compounds with advantageous properties thus extending the pool of reactive liquid crystal compounds available to the expert. Other objects of the present invention can be taken from the following detailed specification.

The present invention thus relates to reactive mesogenic compounds or mixtures thereof obtainable by treating mesogenic diols of formula I, in particular those having a symmetric structure unit with a mixture of halides of formula II and III and to their use in electrooptical systems of scattering type and for the preparation of oriented liquid crystal polymers. The invention furthermore relates to the preparation of compounds according to formula I.

Preferred embodiments of the present invention are:

a) Composition of direactive compounds comprising at least one compound of each formula IV, V and VI,

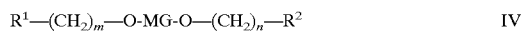
$R^1$—$(CH_2)_m$—O-MG-O—$(CH_2)_n$—$R^2$  IV

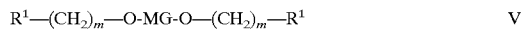
$R^1$—$(CH_2)_m$—O-MG-O—$(CH_2)_m$—$R^1$  V

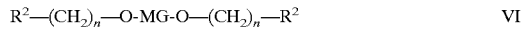
$R^2$—$(CH_2)_n$—O-MG-O—$(CH_2)_n$—$R^2$  VI

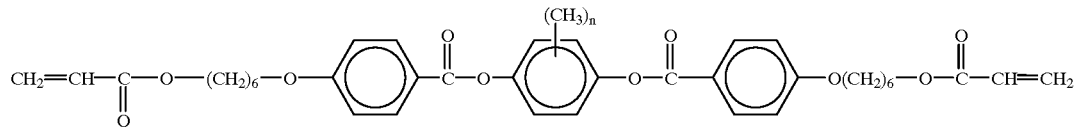

in which MG, m and n have the meaning given, and $R^1$ and $R^2$ are each independently

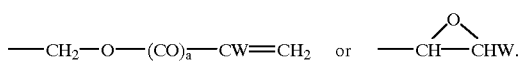

b) Direactive compound or mixture thereof
in which
m−n≧1, in particular 2, 3 or 4.
c) Direactive compound or mixture thereof in which MG is a mesogenic group of formula VIII,

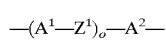   VIII in which
$A^1$ and $A^2$ are each independently
(a) 1,4-phenylene in which one or two CH groups may be replaced by N;
(b) 1,4-cyclohexylene in which one or two non-adjacent $CH_2$ groups may be replaced by —O— or one —CH— group may be replaced by —C(CN)—;
(c) naphthaline-2,6-diyl;
it being possible that group (a) is substituted by halogen cyano or alkyl, alkoxy or alkanoyl with 1 to 6 C atoms,
$Z^1$ is each independently —COO—, —O—CO—, —$CH_2$—$CH_2$—, —C≡C—, —$CH_2$O—, —$OCH_2$— or a single bond, and
o is 1, 2 or 3.
d) Direactive compound or mixture thereof in which MG is selected from the structure elements (1) to (6).

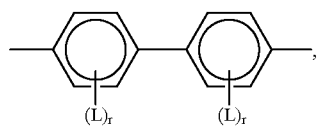   (1)

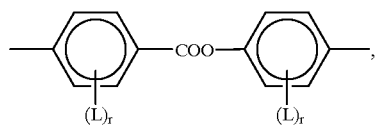   (2)

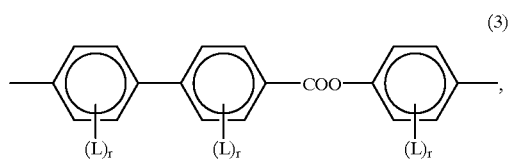   (3)

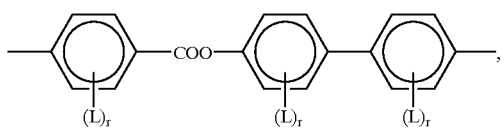   (4)

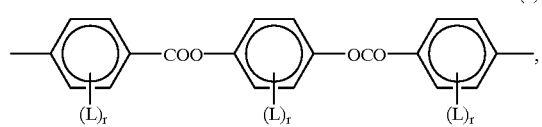   (5)

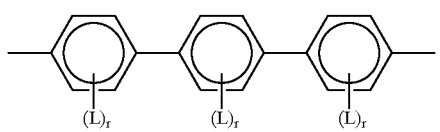   (6)

in which
L is $CH_3$, Cl, F, $OCH_3$ or —CO—$CH_3$, and
r is 0, 1, 2 or 4.
e) Direactive compound or mixture thereof in which n and m are given by the following table:

| m | 5 | 5 | 5 | 4 | 4 |
| n | 2 | 3 | 4 | 2 | 3 |

A further aspect of the present invention is direactive compounds of formula IV A $$R^1—(CH_2)_mO\text{-MG-O}—(CH_2)_n—R^2 \qquad (IVA)$$

in which $R^1$ and $R^2$ have the meaning given, m and n are different integers between 2 and 10, and MG is a mesogenic group, the core of which being symmetrical, preferably a structure element of formula (1), (5) or (6), in particular direactive compounds of the formula IVA1

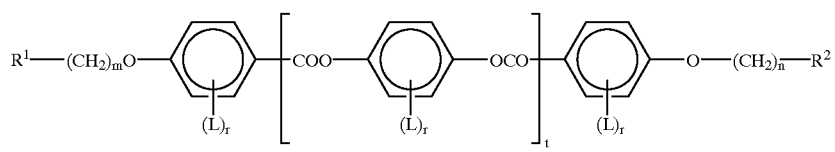

IVA1 in which

R$^1$, R$^2$,

L and r have the meaning given, m and n are different integers between 2 and 10, and t is 0 or 1.

Other aspects of the invention are the polymers prepared by polymerizing a monomer as described above and chemical intermediate compounds or mixtures thereof useful in preparing direactive compounds or mixtures thereof as described above, comprising mesogene-containing molecules, said mesogenes having two side chains attached thereto that contain hydroxyl or vinyl group at the end thereof, said mesogenes and said functional groups being separated by at least two to twenty spacer atoms, wherein both spacer groups have different chain length.

Above and below, the term reactive mesogenic compounds refers to reactive rod-like molecules which may be enantiotropic, monotropic or isotropic, preferably, however, enantiotropic or monotropic.

In the inventive compounds in which MG is a mesogenic group of formula VIII, A$^1$ and A$^2$ can be independently from each other an unsubstituted or a substituted 1,4-phenylene group of formula

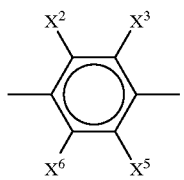

X$^2$, X$^3$, X$^5$ and X$^6$ can be independently from each other H, F, Cl, methyl or CN.

In the following, for the sake of simplicity, the following notation will be used:

Phe. 2 X$^2$ 3 X$^3$ 5 X$^5$ 6 X$^6$ is a 1,4-phenylene group carrying in 2-position the group X$^2$, in 3-position the group X$^3$ etc.; in case X$^2$, X$^3$, X$^5$ and/or X$^6$, denote H, this will not be specified in above notation, i.e. only true substitutions will be listed. Thus Phe, for example, is an unsubstituted 1,4-phenylene group while Phe.2F 5 Cl is a 2-fluoro-5-chloro-1,4-phenylene group. Furthermore, Pyr is pyrimidine-2,5diyl, Pyd is pyridine-2,5-diyl and Nap is a naphthalene-2,6-diyl group. The notation Pyr and Pyd in each case include the 2 possible positional isomers.

The compounds according to formulae IV comprise 2- and 3-ring compounds (n=1 or 2) of formula IV2 and IV3:

R$^1$—(CH$_2$)$_m$—O—A$^1$—Z$^1$—A$^2$—O—(CH$_2$)$_n$—R$^2$       IV2

R$^1$(CH$_2$)$_m$—O—A$^1$—Z$^1$—A$^1$—Z$^1$—A$^2$—O—(CH$_2$)$_n$—R$^2$       IV3

In the 3-ring compounds of formula IV3, the ring groups A$^1$ can be chosen independently from each other.

Especially preferred is a smaller group of 2-ring compounds exhibiting the following structures for —A$^1$—Z$^1$—A$^2$—:

| | |
|---|---|
| -Phe.2CH$_3$-Phe- | IV2-1 |
| -Phe.3CH$_3$-Phe- | IV2-2 |
| -Phe.2Cl-Phe- | IV2-3 |
| -Phe.3Cl-Phe- | IV2-4 |
| -Phe.2CN-Phe- | IV2-5 |
| -Phe.3CN-Phe- | IV2-6 |
| -Phe.2Cl3Cl-Phe- | IV2-7 |
| -Phe.2Cl3F-Phe- | IV2-8 |
| -Phe.2F-Phe- | IV2-9 |
| -Phe.3F-Phe- | IV2-10 |
| -Phe.-Phe- | IV2-11 |
| -Phe.F-Nap- | IV2-12 |
| -Phe.2Cl-Nap- | IV2-13 |
| -Phe.F-Nap- | IV2-14 |
| -Phe.3Cl-Nap- | IV2-15 |
| -Phe.2F-Pyr- | IV2-16 |
| -Phe.2F-Pyr- | IV2-17 |
| -Phe.2CH$_3$-Pyd- | IV2-18 |
| -Phe.2Cl-Pyd- | IV2-19 |
| -Phe.F—CH$_2$CH$_2$-Phe- | IV2-20 |
| -Phe.3F—CH$_2$CH$_2$-Phe- | IV2-21 |
| -Phe.2Cl—CH$_2$CH$_2$-Phe- | IV2-22 |
| -Phe.3Cl—CH$_2$CH$_2$-Phe- | IV2-23 |
| -Phe.2CN—CH$_2$CH$_2$-Phe- | IV2-24 |
| -Phe.3CN—CH$_2$CH$_2$-Phe- | IV2-25 |
| -Phe.2Cl3Cl—CH$_2$CH$_2$-Phe- | IV2-26 |
| -Phe.2Cl3F—CH$_2$CH$_2$-Phe- | IV2-27 |

The 3-ring compounds according to formula IV3 preferably exhibit the following structures for —A$^1$—Z$^1$—A$^1$—Z$^1$—A$^2$:

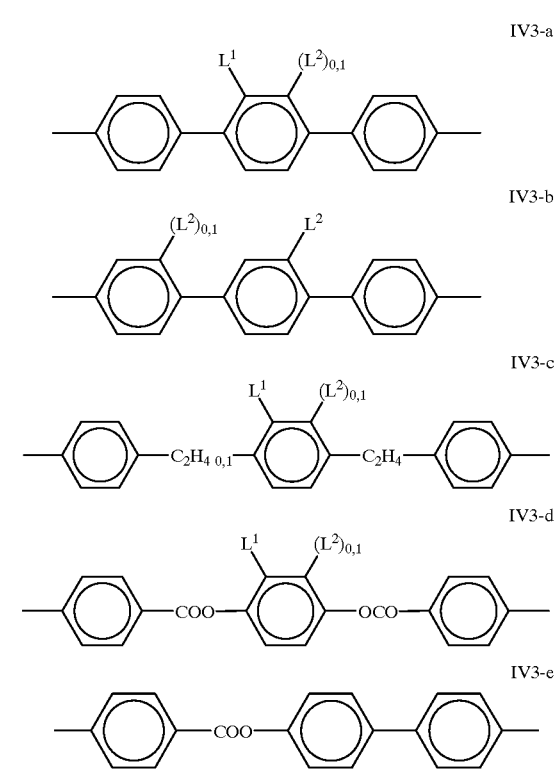

In these structures, IV3-a to IV3-d, L$^1$ and L$^2$ denote independently from each other H, —Cl, —F, —CN and C$_r$H$_{2r+1-s}$ and, in particular, —Cl, —F, —CN, —CH$_3$, and/or —C$_2$H$_5$.

Especially preferred are the following patterns:

| | |
|---|---|
| -Phe-Phe.2CH$_3$-Phe- | IV3-a-1 |
| -Phe-Phe.2Cl-Phe- | IV3-a-2 |

-continued

| | |
|---|---|
| -Phe-Phe.2CN-Phe- | IV3-a-3 |
| -Phe-Phe.2F-Phe- | IV3-a-4 |
| -Phe-Phe-Phe- | IV3-a-5 |
| -Phe-Phe.2C$_2$H$_5$-Phe- | IV3-a-6 |
| -Phe-Phe.3CH$_3$-Phe- | IV3-b-1 |
| -Phe-Phe.3Cl-Phe- | IV3-b-2 |
| -Phe-Phe.3CN-Phe- | IV3-b-3 |
| -Phe-Phe.3F-Phe- | IV3-b-4 |
| -Phe-Phe.3C$_2$H$_5$-Phe- | IV3-b-5 |
| -Phe.3F-Phe.3Cl-Phe- | IV3-b-6 |
| -Phe.3F-Phe.3CH$_3$-Phe- | IV3-b-7 |
| -Phe.3Cl-Phe.3Cl-Phe- | IV3-b-8 |
| -Phe.3Cl-Phe.3CH$_3$-Phe- | IV3-b-9 |
| -Phe-Phe.2Cl-Phe.3Cl— | IV3-b-10 |
| -Phe-Phe.3Cl-Phe.3Cl— | IV3-b-11 |
| -Phe-Phe.2Cl-Phe.2Cl— | IV3-b-12 |
| -Phe-Phe.3Cl-Phe.2Cl— | IV3-b-13 |
| -Phe-Phe.2CH$_3$-Phe.3Cl— | IV3-b-14 |
| -Phe-Phe.3CH$_3$-Phe.3Cl— | IV3-b-15 |
| -Phe-Phe.2CH$_3$-Phe.2Cl— | IV3-b-16 |
| -Phe-Phe.3CH$_3$-Phe.2Cl— | IV3-b-17 |
| -Phe-Phe.2F-Phe.3Cl— | IV3-b-18 |
| -Phe-Phe.3F-Phe.3Cl— | IV3-b-19 |
| -Phe-Phe.2F-Phe.2Cl— | IV3-b-20 |
| -Phe-Phe.3F-Phe.2Cl— | IV3-b-21 |
| -Phe-Phe.2Cl-Phe.3CN— | IV3-b-22 |
| -Phe-Phe.3Cl-Phe.3CN— | IV3-b-23 |
| -Phe-Phe.2Cl-Phe.2CN— | IV3-b-24 |
| -Phe-Phe.3Cl-Phe.2CN— | IV3-b-25 |
| -Phe-Phe.2CH$_3$-Phe.3CN— | IV3-b-26 |
| -Phe-Phe.3CH$_3$-Phe.3CN— | IV3-b-27 |
| -Phe-Phe.2CH$_3$-Phe.2CN— | IV3-b-28 |
| -Phe-Phe.3CH$_3$-Phe.2CN— | IV3-b-29 |
| -Phe-Phe.3F-Phe.3CN— | IV3-b-30 |
| -Phe-Phe.2F-Phe.3CN— | IV3-b-31 |
| -Phe-Phe.3F-Phe.2CN— | IV3-b-32 |
| -Phe-Phe.2F-Phe.2CN— | IV3-b-33 |
| -Phe-Phe.2F-Phe.2F— | IV3-b-34 |
| -Phe-Phe.3F-Phe.3F— | IV3-b-35 |
| -Phe-Phe.2CH$_3$—C$_2$H$_4$-Phe- | IV3-c-1 |
| -Phe-Phe.2Cl—C$_2$H$_4$-Phe- | IV3-c-2 |
| -Phe-Phe.2CN—C$_2$H$_4$-Phe- | IV3-c-3 |
| -Phe-Phe.2F—C$_2$H$_4$-Phe- | IV3-c-4 |
| -Phe-Phe.2C$_2$H$_5$—C$_2$H$_4$-Phe- | IV3-c-5 |
| -Phe-Phe.2Cl3F—C$_2$H$_4$-Phe- | IV3-c-6 |
| -Phe-Phe.2Cl3Cl—C$_2$H$_4$-Phe- | IV3-c-7 |
| -Phe-C$_2$H$_4$-Phe.2CH$_3$—C$_2$H$_4$-Phe- | IV3-c-8 |
| -Phe-C$_2$H$_4$-Phe.2Cl—C$_2$H$_4$-Phe- | IV3-c-9 |
| -Phe-C$_2$H$_4$-Phe.2CN—C$_2$H$_4$-Phe- | IV3-c-10 |
| -Phe-C$_2$H$_4$-Phe.F—C$_2$H$_4$-Phe- | IV3-c-11 |
| -Phe-C$_2$H$_4$-Phe.2OCF$_3$—C$_2$H$_4$-Phe- | IV3-c-12 |
| -Phe-COO-Phe.OCO-Phe- | IV3-d-1 |
| -Phe-COO-Phe.2CH$_3$—OCO-Phe- | IV3-d-2 |
| -Phe-COO-Phe.3CH$_3$—OCO-Phe- | IV3-d-3 |
| -Phe-COO-Phe.2CH$_3$3CH$_3$—OCO-Phe- | IV3-d-4 |
| -Phe-COO-Phe.2OCH$_3$—OCO-Phe- | IV3-d-5 |
| -Phe-COO-Phe.2Cl—OCO-Phe- | IV3-d-6 |
| -Phe-COO-Phe.2F—OCO-Phe- | IV3-d-7 |
| -Phe-COO-Phe.2F3F—OCO-Phe- | IV3-d-8 |
| -Phe-COO-PhePhe- | IV3-e-1 |
| -Phe-COO-Phe.2FPhe- | IV3-e-2 |
| -Phe-COO-Phe.3FPhe- | IV3-e-3 |
| -Phe-COO-PhePhe.2F— | IV3-e-4 |
| -Phe-COO-PhePhe.3F— | IV3-e-5 |
| -Phe.2F—COO-PhePhe- | IV3-e-6 |
| -Phe.3F—COO-PhePhe- | IV3-e-7 |

It was observed that the stability of 3-ring compounds wherein one of the 2 groups $Z^1$ is —COO— or —OCO— while the other denotes a single bond, can be increased if the compound is laterally di- or higher substituted, particularly di-substituted by —Cl, —F, —CN and/or —CH$_3$. Compounds of this type are preferred.

Especially preferred are further 3-ring compounds where both groups $Z^1$ are either —COO—, or —OCO— and at least one of the rings $A^1$, $A^{1'}$ and $A^2$ are at least mono substituted.

In the compounds of formula IV $R^1$ is CH$_2$=CW—COO—CH$_2$—, CH$_2$=CH—O—CH$_2$—

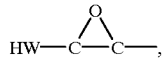, with W being H, Cl or alkyl with 1–5 C atoms and m being 1–7.

Preferably, $R^1$ and $R^2$ is a vinyl group, an acrylate group, an epoxy group and especially preferred are the following means of $R^1$ and $R^2$:

$$CH_2\!=\!CH\!-\!COO\!-\!CH_2\!- \quad R^1\text{-}1$$

  R$^1$-2

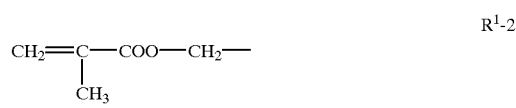  R$^1$-3

$$CH_2\!=\!CH\!-\!O\!-\!CH_2\!- \quad R^1\text{-}4$$

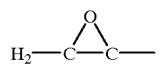  R$^1$-5 with alkyl denoting C$_1$–C$_3$-alkyl and m being 1–5.

The reaction methods mentioned are briefly summarized in the following synthetic tree:

Scheme I

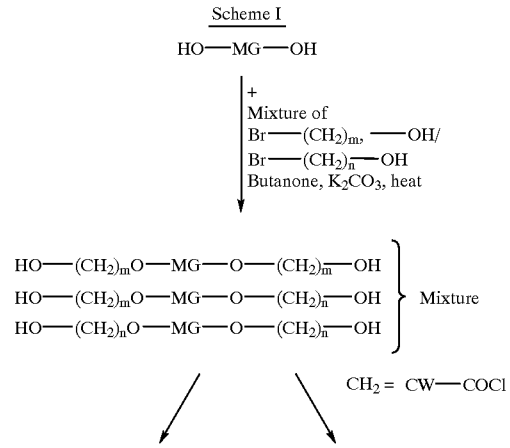

Butylvinyl ether
DCM
1, 10-Phenanthroline
Pd (II)-Acetate

Mixture of
"Divinylethers"

Mixture of
"diacrylates"

DCM = dichloromethane

Scheme II
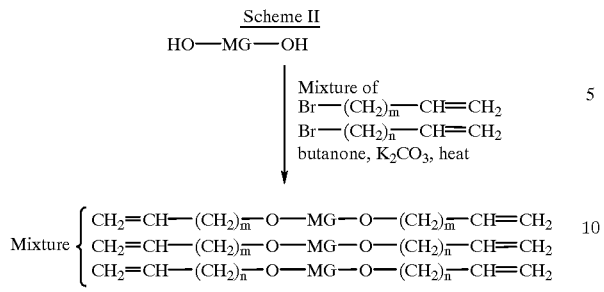
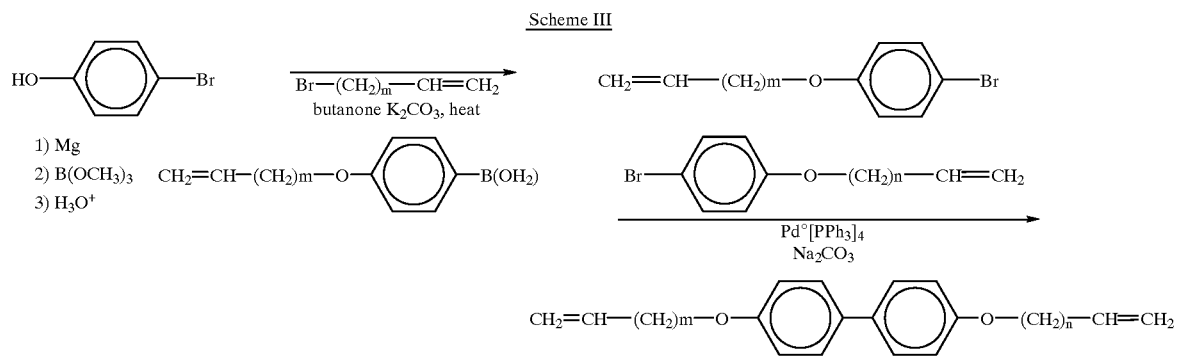
Certain compounds or mixtures according to the invention are obtainable in a "one-pot-synthesis" as outlined in scheme IV:
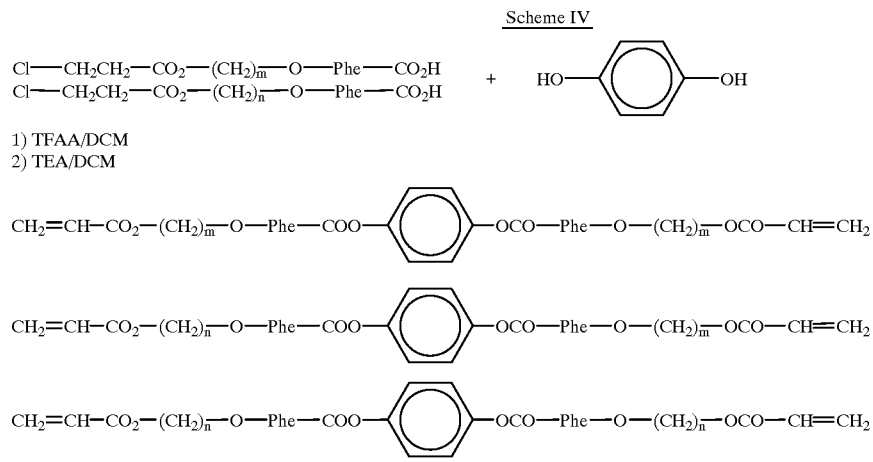
TFAA = trifluoroacetic acid
TEA = triethylamine
Individual compounds of this type can be obtained according to schemes V to VII:

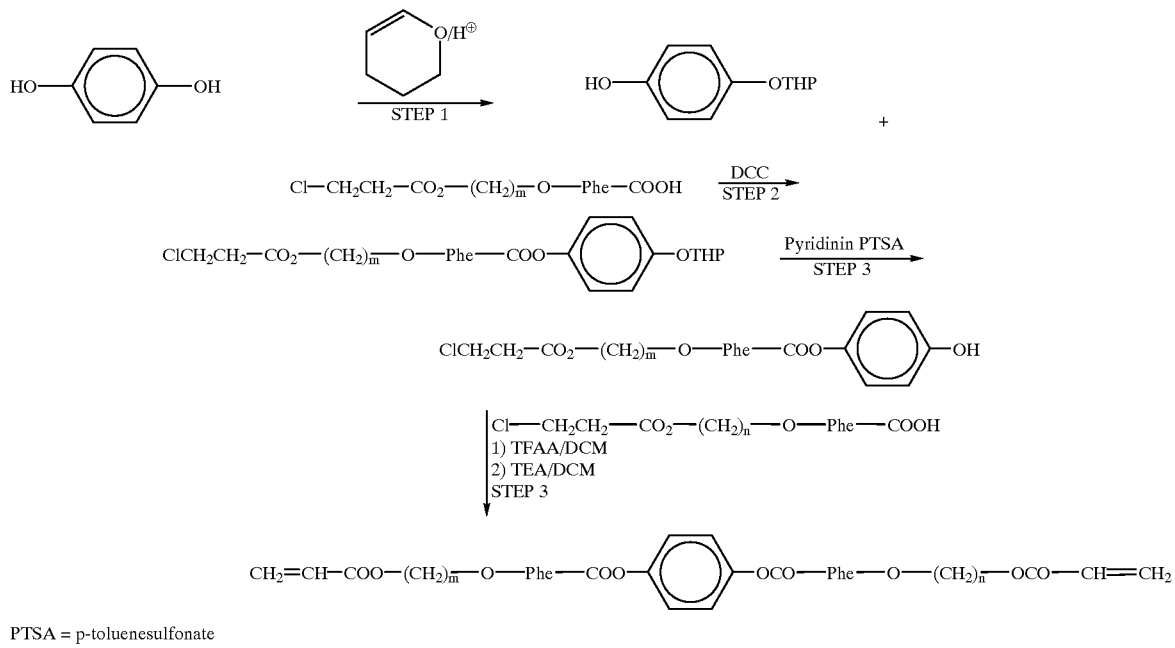
PTSA = p-toluenesulfonate
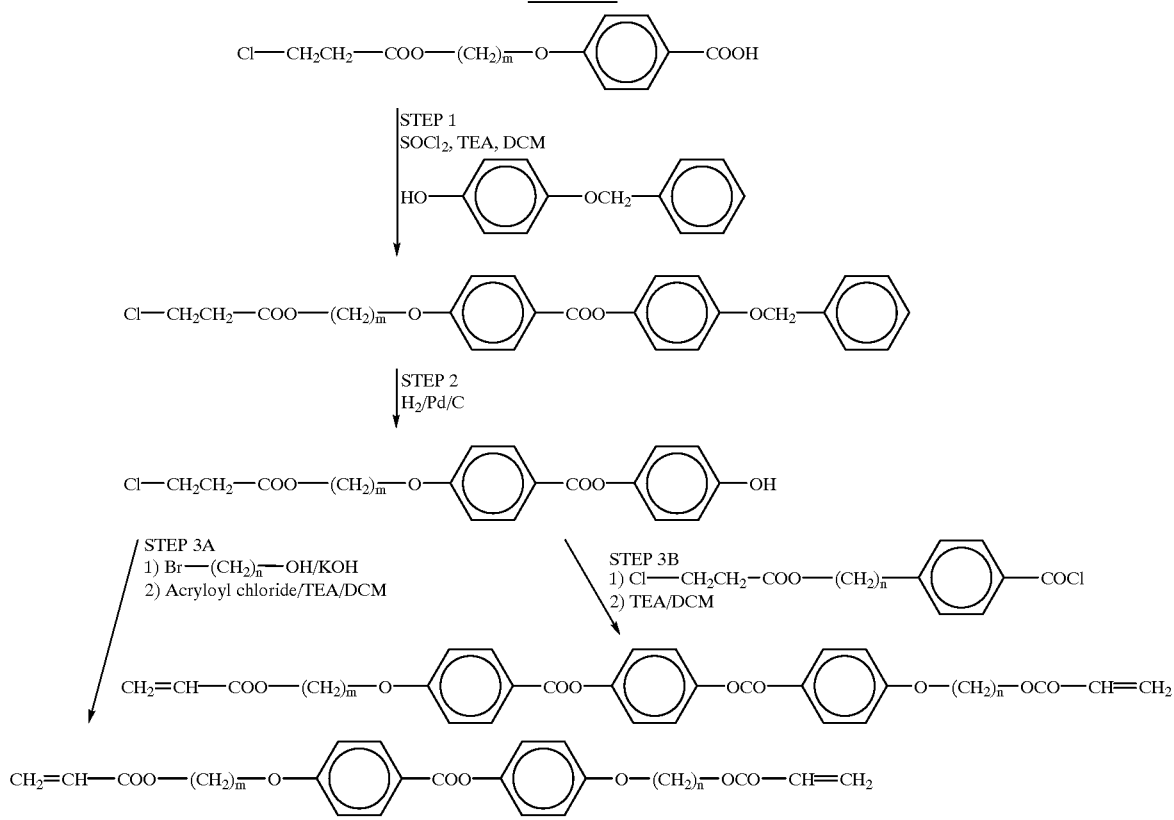

Scheme VII

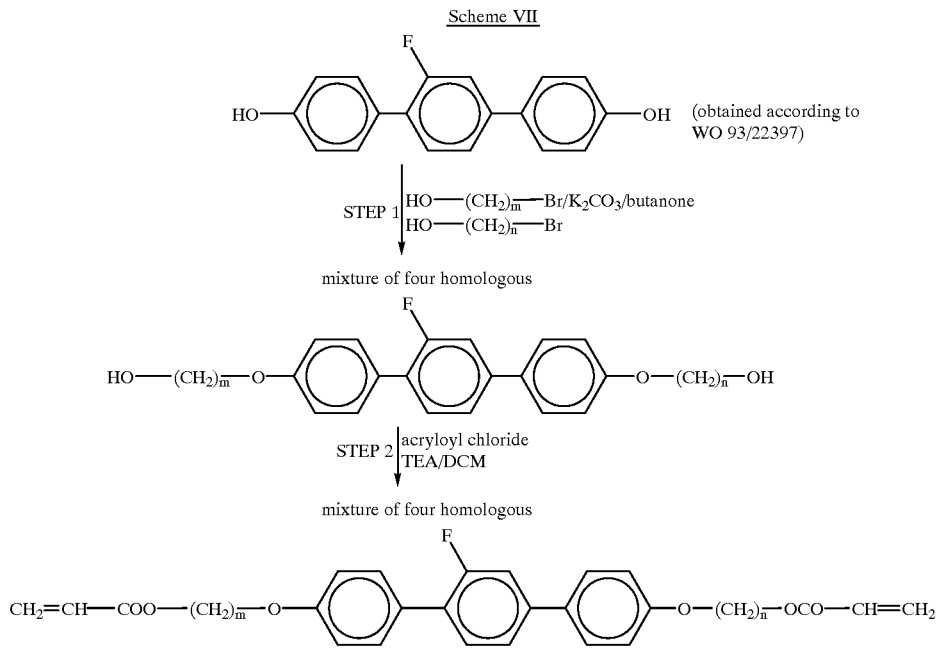

The reaction schemes mentioned above are to illustrate the invention without restricting it. The expert can choose other reaction methods without any inventive efforts.

In the following and in the preceding, all percentages given are percentages by weight. Temperatures are given in degrees Celsius.

The following examples are intended to illustrate the invention without restricting it.

EXAMPLE 1

The reactive liquid crystalline compound (1)

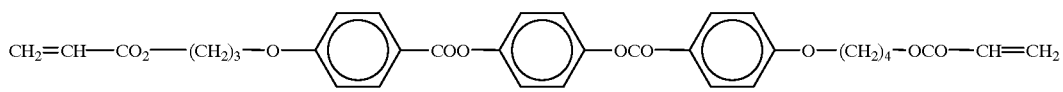

is prepared via the sequence of reaction steps shown in scheme V. In step 4 of scheme V 2.2 moles TFAA are added dropwise to a solution 2 moles of the phenol obtained in step 3 of scheme V and 2 moles of the benzoic acid in 2 l of DCM.

The reaction mixture is stirred at room temperature for 16 hours. Then 5 moles of TEA in 1 l of DCM are added. The mixture is stirred for 16 hours. Aqueous work-up and column chromatography give (1) which shows K 111 S.

The following compounds are obtained analogously:

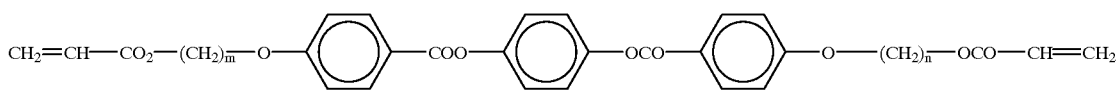

| Compound No. | m | n | phase transition temperature (° C.) |
|---|---|---|---|
| (2) | 3 | 5 | K 76 N 160 I |
| (3) | 4 | 5 | K 67 N 165 I |
| (4) | 4 | 6 | K 78 S 82 N 159 I |
| (5) | 5 | 6 | K 78 S 80 N 162 I |
| Comp 1 | 4 | 4 | K 105 N 164 I |
| Comp 2 | 5 | 5 | K 91 N 167 I |
| Comp 3 | 6 | 6 | K 105 (S 95) 152 I |

EXAMPLE 2

A mixture of 1 mol

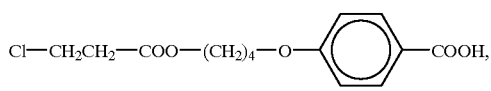

1 mol

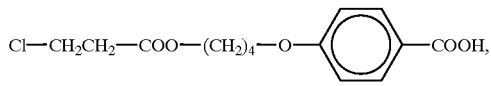

and 1 mol p-hydroquinone is treated with 22 moles of TFAA followed by 2.5 moles of TEA.

A mixture consisting of 1 part comp 1 and 1 part comp 3 and 2 parts of Compound No. (4) is obtained which shows a melting point of 56° C. and a clearing point of 163° C.

Analogously a mixture of the following compounds is obtained:

1 part of

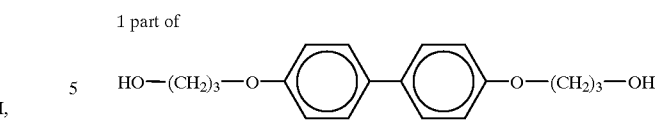

1 part of

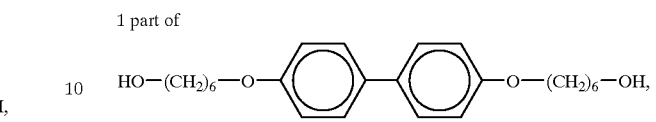

and 2 part of

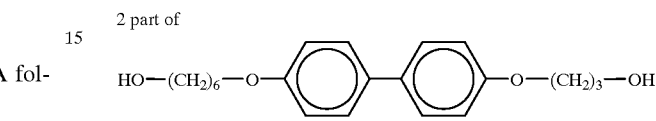

is obtained.

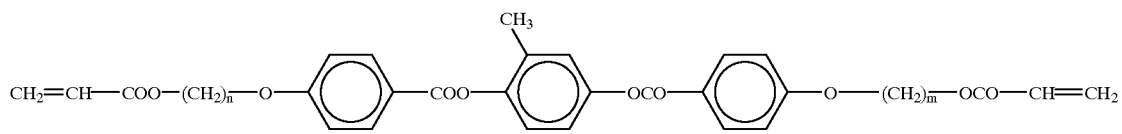

| n | m | parts |
|---|---|-------|
| 3 | 3 | 1 |
| 6 | 6 | 1 |
| 3 | 6 | 1 |
| 6 | 3 | 1 |

This composition shows a melting point below 30° C. and a clearing point of 119° C.

EXAMPLE 3

A mixture of 0.5 moles of biphenol, 1.3 moles of potassium hydroxide, 0.6 moles of 3-bromopropanol and 0.6 moles of 3 bromohexanol is heated in 2 liters of butanone for 16 hrs. After aqueous work-up a mixture of This mixture is treated with 1.2 moles of acryloyl chloride and 1.2 moles of TEA in 1.5 liters of dichloroethane DCM and refluxed for 3 hours.

After aqueous work-up the resulting reactionmixture is purified by column-chromatography to yield a mixture of diacrylates (6), (7) and (8).

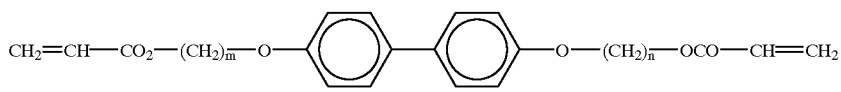

| Compound No. | m | n | parts |
|--------------|---|---|-------|
| (6) | 3 | 3 | 1 |
| (7) | 5 | 6 | 1 |
| (8) | 3 | 6 | 2 |

Analogously a mixture of compounds of formulae (9), (10), (11) and (12) is obtained

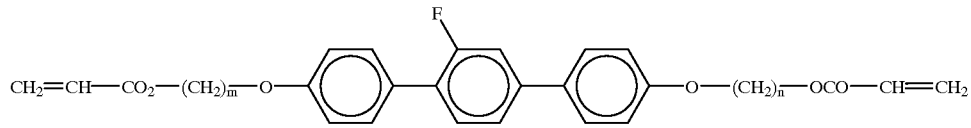

| Compound No. | m | n | parts |
|---|---|---|---|
| (9) | 3 | 3 | 1 |
| (10) | 6 | 6 | 1 |
| (11) | 3 | 6 | 1 |
| (12) | 6 | 3 | 1 |

What is claimed is:

1. A mixture of three or more direactive mesogenic compounds, which comprises at least one compound of each of the formulae IV, V and VI, $$R^1-(CH_2)_m-O-MG-O-(CH_2)_n-R^2 \quad \text{IV}$$

$$R^1-(CH_2)_m-O-MG-O-(CH_2)_m-R^1 \quad \text{V}$$

$$R^2-(CH_2)_n-O-MG-O-(CH_2)_n-R^2 \quad \text{VI}$$

in which MG is a mesogenic group, m and n are different integers from 1 to 20, and $R^1$ and $R^2$ are each independently

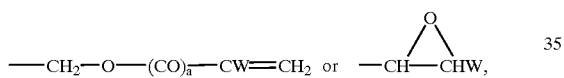

in which a is 0 or 1 and W is H, $CH_3$ or Cl, wherein said mesogenic compounds are obtained by c) treating a mesogenic diol of formula I, $$HO-MG-OH \quad (I)$$

with a mixture of the halides of formulae II and III, $$X^1-(CH_2)_m-R^a \quad (II)$$

$$X^2-(CH_2)_n-R^b \quad (III)$$

in the presence of a base
wherein $X^1$ and $X^2$ are each independently Cl, Br or I,
$R^a$ and $R^b$ are each independently $-CH_2OH$ or $-CH=CWH$
and MG, W, m and n have the meaning given, and d) treating the resulting intermediate
in the case of $R^a$ and $R^b$ being $-CH_2OH$, with a vinyl derivative of formula $CH_2=CW-(CO)_a-O-$ or a reactive derivative thereof,
in the case of $R^a$ and $R^b$ being $-CH=CWH$ with a perbenzoic acid.

2. A mixture of three or more direactive compounds according to claim 1, in which
MG is a mesogenic group of formula VIII, $$-(A^1-Z^1)_o-A^2- \quad \text{VIII}$$

in which
$A^1$ and $A^2$ are each independently
(a) 1,4-phenylene in which one or two CH groups may be replaced by N;
(b) 1,4-cyclohexylene in which one or two non-adjacent $CH_2$ groups may be replaced by $-O-$ or one $-CH-$ group may be replaced by $-C(CN)-$;
(c) naphthaline-2,6-diyl;
wherein optionally the (a) group is substituted by halogen, cyano or alkyl with 1 to 6 C atoms, $Z^1$ is each independently $-COO-$, $-O-CO-$, $-CH_2-CH_2-$, $-C\equiv C-$, $-CH_2O-$, $-OCH_2-$ or a single bond, and o is 1, 2 or 3.

3. A mixture of two or more direactive compounds according to claim 1, in which MG is selected from

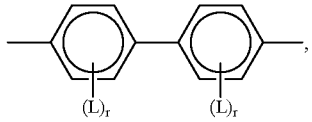  (1)

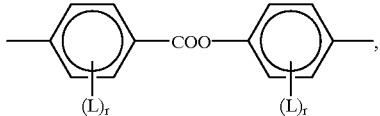  (2)

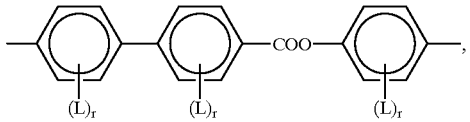  (3)

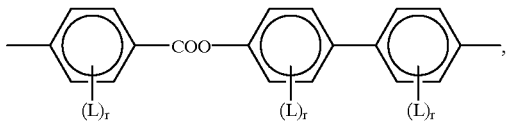  (4)

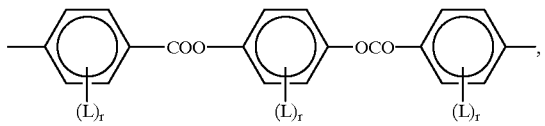  (5)

or

-continued

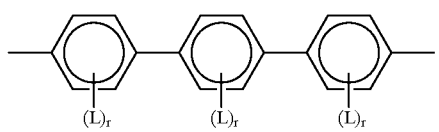
(6)

in which

L is $CH_3$, Cl, F, $OCH_3$ or $—CO—CH_3$, and r is 0, 1, 2 or 4.

4. A mixture of three or more direactive compounds according to claim 1, in which n and m are given by the following table:

| m | 5 | 5 | 5 | 4 | 4 |
|---|---|---|---|---|---|
| n | 2 | 3 | 4 | 2 | 3 |

5. A mixture of two or directive compounds according to claim 1, in which $m-n \geq 1$.

6. A polymer obtained by polymerizing a mixture according to claim 1.

7. A mixture of chemical intermediate compounds useful in preparing a mixture of direactive compounds according to claim 1, comprising mesogene-containing molecules, said mesogenes having two side chains attached thereto that contain a hydroxyl or vinyl group at the ends thereof, said mesogenes and said functional groups being separated by at least two to twenty spacer atoms, wherein both spacer groups have different chain length, which mixture is obtained by a) treating a mesogenic diol of formula I,

HO-MG-OH (I)

with a mixture of the halides of formulae II and III, $X^1—(CH_2)_m—R^a$ (II)

$X^2—(CH_2)_n—R^b$ (III)

in the presence of base
in which
MG is a mesogenic group,
$X^1$ and $X^2$ are each independently Cl, Br or I,
m and n are different integers from 1 to 20, and
$R^a$ and $R^b$ are each independently groups selected from
$—CH_2OH$ or $—CH=CWH$
wherein
W is H, $CH_3$ or Cl.

8. A mixture of three or more direactive compounds according to claim 2, wherein at least one MG group is a three ring group wherein one of the two $Z^1$ groups is —COO— or —OCO—, the other is a single bond and there are at least two lateral —Cl, —F, —CN or —$CH_3$ ring substituents.

9. A mixture of three or more direactive mesogenic compounds of claim 1, wherein the method of obtaining the compound(s) is a one-pot synthesis.

10. A composition of claim 1, wherein MG is selected from

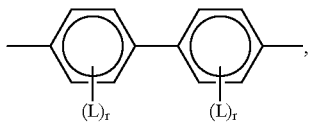
(1)

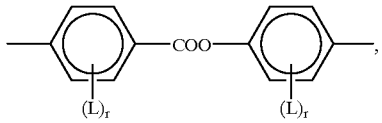
(2)

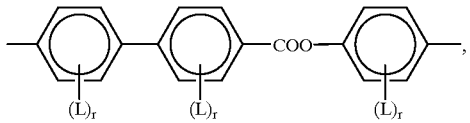
(3)

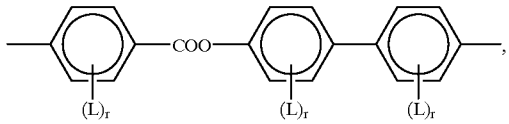
(4)

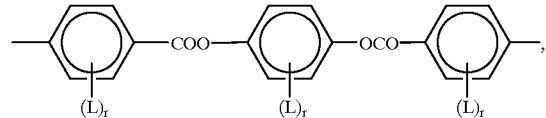
(5)

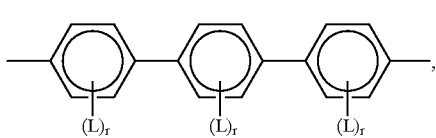

or

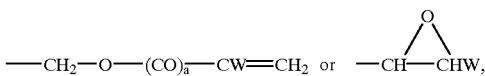
(6)

wherein L is $CH_3$, CL, F, $OCH_3$ or $—CO—CH_3$ and r is 0, 1, 2 or 4.

11. A composition comprising direactive compounds which comprises at least one compound of each of the formulae IV, V and VI $R^1—(CH_2)_m—O-MG-O—(CH_2)_n—R^2$     IV $R^1—(CH_2)_m—O-MG-O—(CH_2)_m—R^1$     V $R^2—(CH_2)_n—O-MG-O—(CH_2)_n—R^2$     VI in which MG is a mesogenic group, m and n are different integers from 1 to 20, and $R^1$ and $R^2$ are each independently

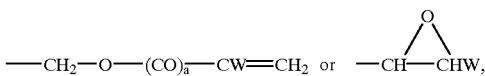

in which a is 0 or 1 and W is H, $CH_3$ or Cl, wherein MG is not

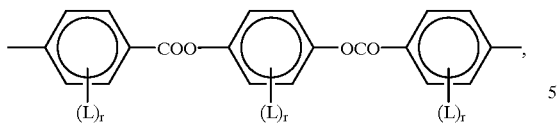

wherein L is CH3, CL, F, OCH3 or —CO—CH3 and r is 0, 1, 2 or 4.

wherein L is CH3, CL, F, OCH3 or —CO—CH3 and r is 0, 1, 2 or 4.

12. A composition of claim 11, comprising three or more direactive compounds of the formula $R^1$—$(CH_2)_m$O-MG-O—$(CH_2)_n$—$R^2$ wherein m, n, $R^1$, $R^2$ and MG are as defined in claim 11.

13. A polymer obtained by polymerizing a composition according to claim 11, which is an oriented liquid crystalline polymer.

14. An electrooptical scattering system which contains an oriented liquid crystalline polymer according to claim 13.

15. A composition of claim 11, wherein m−n≧1.

16. A composition of claim 12, wherein MG is a mesogenic group of formula VIII, $$—(A^1—Z^1)_o—A^2— \qquad \text{VIII}$$

in which $A^1$ and $A^2$ are each independently
  (a) 1,4-phenylene in which one or two CH groups may be replaced by N;
  (b) 1,4-cyclohexylene in which one or two non-adjacent $CH_2$ groups may be replaced by —O— or one —CH— group may be replaced by —C(CN)—; or
  (c) napthalene-2,6-diyl,
    wherein optionally group (a) is substituted by halogen, cyano, alkyl, alkoxy or alkanoyl with 1 to 6 carbon atoms,
    each $Z^1$ is independently —COO—, —O—CO—, —$CH_2CH_2$— —C≡C—, —$CH_2$O—, —$OCH_2$—or a single bond, and
    o is 1, 2 or 3.

17. A composition of claim 12, wherein n and m are given by the following table:

| m | 5 | 5 | 5 | 4 | 4 |
|---|---|---|---|---|---|
| n | 2 | 3 | 4 | 2 | 3. |

18. A polymer obtained by addition polymerization of a compound according to claim 11.

19. A method for preparing a mixture of three or more direactive mesogenic compounds which comprises:

a) treating a mesogenic diol of formula I,

HO-MG-OH  (I)

with a mixture of the halides of formulae II and III, $X^1$—$(CH_2)_m$—$R^a$  (II)

$X^2$—$(CH_2)_n$—$R^b$  (III)

in the presence of a base,
in which
  MG is a mesogenic group,
  $X^1$ and $X^2$ are each independently Cl, Br or I,
  m and n are different integers from 1 to 20, and
  $R^a$ and $R^b$ are each independently groups selected from
    —$CH_2$OH or —CH═CWH
    wherein
      W is H, $CH_3$ or Cl, and
b) treating the resulting intermediate
  in the case of $R^a$ and $R^b$ being —$CH_2$OH, with a vinyl derivative of formula $CH_2$═CW—$(CO)_a$—O— or a reactive derivative thereof, in which a is 0 or 1
  in the case of $R^a$ and $R^b$ being —CH═CWH with a perbenzoic acid.

20. The method of claim 19, wherein
MG is a mesogenic group of formula VIII, $$—(A^1—Z^1)_o—A^2— \qquad \text{VIII}$$

in which
$A^1$ and $A^2$ are each independently
  (a) 1,4-phenylene in which one or two CH groups may be replaced by N;
  (b) 1,4-cyclohexylene in which one or two non-adjacent $CH_2$ groups may be replaced by —O— or one —CH— group may be replaced by —C(CN)—;
  (c) naphthaline-2,6-diyl;
    wherein optionally the (a) group is substituted by halogen, cyano or alkyl with 1 to 6 C atoms,
$Z^1$ is each independently —COO—, —O—CO—, —$CH_2$—$CH_2$—, —C≡C—, —$CH_2$O—, —$OCH_2$— or a single bond, and
o is 1, 2 or 3.

21. The method of claim 19, wherein MG is (1)
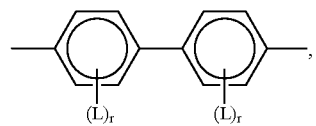

(2)
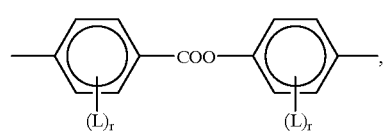

(3)
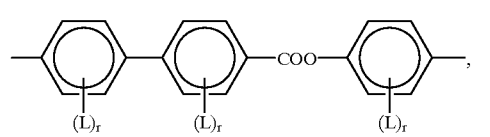

(4)
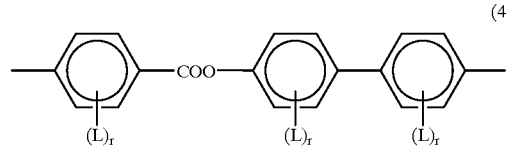

(5)
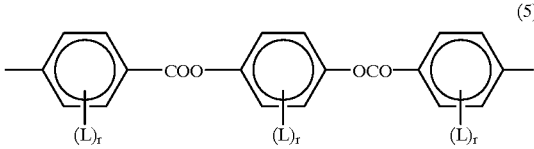

or

-continued
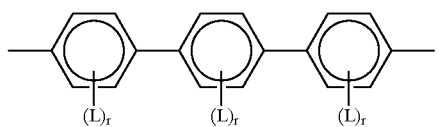
(6)
in which
L is $CH_3$, Cl, F, $OCH_3$ or —CO—$CH_3$, and
r is 0, 1, 2 or 4.
22. The method of claim 19, wherein n and m are given by the following table:
| m | 5 | 5 | 5 | 4 | 4 |
|---|---|---|---|---|---|
| n | 2 | 3 | 4 | 2 | 3. |
23. The method of claim 19, wherein the method is carried out in a one-pot synthesis.
* * * * *